US00PP21733P3

(12) United States Plant Patent
Andersen

(10) Patent No.: US PP21,733 P3
(45) Date of Patent: Feb. 22, 2011

(54) ***CAMPANULA* PLANT NAMED 'CBO 1'**

(50) Latin Name: *Campanula portenschlagiana*
Varietal Denomination: CBO 1

(75) Inventor: Jørgen Kurt Andersen, Odense SO (DK)

(73) Assignee: Gartneriet Thoruplund A/S, Odense SO (DK)

( * ) Notice: Subject to any disclaimer, the term of this patent is extended or adjusted under 35 U.S.C. 154(b) by 0 days.

(21) Appl. No.: 12/459,165

(22) Filed: Jun. 26, 2009

(65) Prior Publication Data

US 2010/0333245 P1 Dec. 30, 2010

(51) Int. Cl.
*A01H 5/00* (2006.01)

(52) U.S. Cl. ..... Plt./414

(58) Field of Classification Search ..... Plt./263, Plt./414

See application file for complete search history.

(56) References Cited

PUBLICATIONS

UPOV-ROM GTITM, Plant Variety Database, 2010/03, GTI Jouve Retrieval Software, citation for *Campanula*, 'CBO 1'.*

Print-out of application number and filing date from Community Plant Variety Office (CPVO) website for corresponding, CPVO application No. 2006/2594 filed Jun. 12, 2006 (5 pages). (http://www.cpvoextranet.cpvo.europa.eu).

* cited by examiner

*Primary Examiner*—Susan B McCormick Ewoldt
(74) *Attorney, Agent, or Firm*—Foley & Lardner LLP

(57) ABSTRACT

A new and distinct cultivar of *Campanula* plant named 'CBO 1', characterized by its upright to spreading plant habit; dense and bushy plant form, mainly due to less upright stems; vigorous growth habit; no need for vernalization for flower induction; shorter cultivation period; and single, violet colored bell-shaped flowers.

3 Drawing Sheets

Latin name of genus and species of the plant claimed: *Campanula portenschlagiana.*

Variety denomination: 'CBO 1'.

BACKGROUND OF THE INVENTION

The present invention relates to a new and distinct cultivar of *Campanula* plant, botanically known as *Campanula portenschlagiana* Schult., commonly known as Dalmatian Bellflower, and hereinafter referred to by the name 'CBO 1'.

The new *Campanula*, 'CBO 1', is a product of a planned breeding program conducted by the inventor, Jörgen Kurt Andersen, in Fraugde, Denmark. The objective of the breeding program is to develop a new *Campanula* cultivar with upright to spreading, plant habit and unique colored flowers.

The new *Campanula*, 'CBO 1' originated from a chemically-induced mutation of an unpatented cultivar from the proprietary breeding line of *Campanula portenschlagiana* Schult. designated '2502'. The new *Campanula* 'CBO 1' was discovered and selected by the inventor as a single flowering plant in April of 2004 in a controlled environment in Fraugde, Denmark. The inventor selected 'CBO 1' on the basis of its upright to spreading plant habit and violet flowers.

Asexual reproduction of the new *Campanula* cultivar by terminal cuttings was first performed in April 2005 in Fraugde, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'CBO 1'. These characteristics in combination distinguish 'CBO 1' as a new and distinct cultivar:

1. Upright to spreading plant habit;
2. Dense and bushy plant form, mainly due to less upright stems;
3. Vigorous growth habit;
4. No need for vernalization for flower induction;
5. Shorter cultivation period; and
6. Single, violet colored bell-shaped flowers.

Plants of the instant cultivar 'CBO 1' differ primarily from plants of the parent, an unpatented cultivar from the proprietary breeding line of *Campanula portenschlagiana* Schult. designated '2502', in the following characteristics:

1. plants of 'CBO 1' produce flowers in a shorter cultivation period (about 14 weeks) than plants of '2502' (about 16 weeks);
2. plants of the 'CBO 1' produce more flowers per lateral stem (about 8 to 10, arranged upright to outward) than plants of '2502' (about 4 to 6, arranged upright);
3. plants of the 'CBO 1' produce darker violet mature petals (upper side: RHS 86B) than plants of '2502' (upper side: RHS N87D);
4. plants of the 'CBO 1' produce sepals which are 1) larger (length: about 5 mm to 6 mm; width: about 2 mm) and 2) differ in color (mature, upper side: yellow-green, RHS 146A, and gray-purple, RHS 184B, near tips) than plants of '2502' (sepals are 1) smaller (length: about 3 mm to 4 mm; width: about 1 mm) and 2) green in color (mature, upper side: RHS 1138A);

5. plants of 'CBO 1' are flatter in overall plant shape (flat, globular shape with ascending floral stems) than plants of '2502' (globular shape with upright stems); and
6. plants of the 'CBO 1' produce darker yellow-green mature leaves (upper side: RHS 147C) than plants of '2502' (upper side: RHS 146C).

BRIEF DESCRIPTION OF THE PHOTOGRAPHS

The accompanying colored photographs illustrate the overall appearance of the new *Campanula* 'CBO 1', showing the colors as true as it is reasonably possible to obtain in colored reproductions of this type. Colors in the photographs may differ slightly from the color values cited in the detailed botanical description, which more accurately describe the actual colors of 'CBO 1'.

DETAILED BOTANICAL DESCRIPTION

Figure 1:
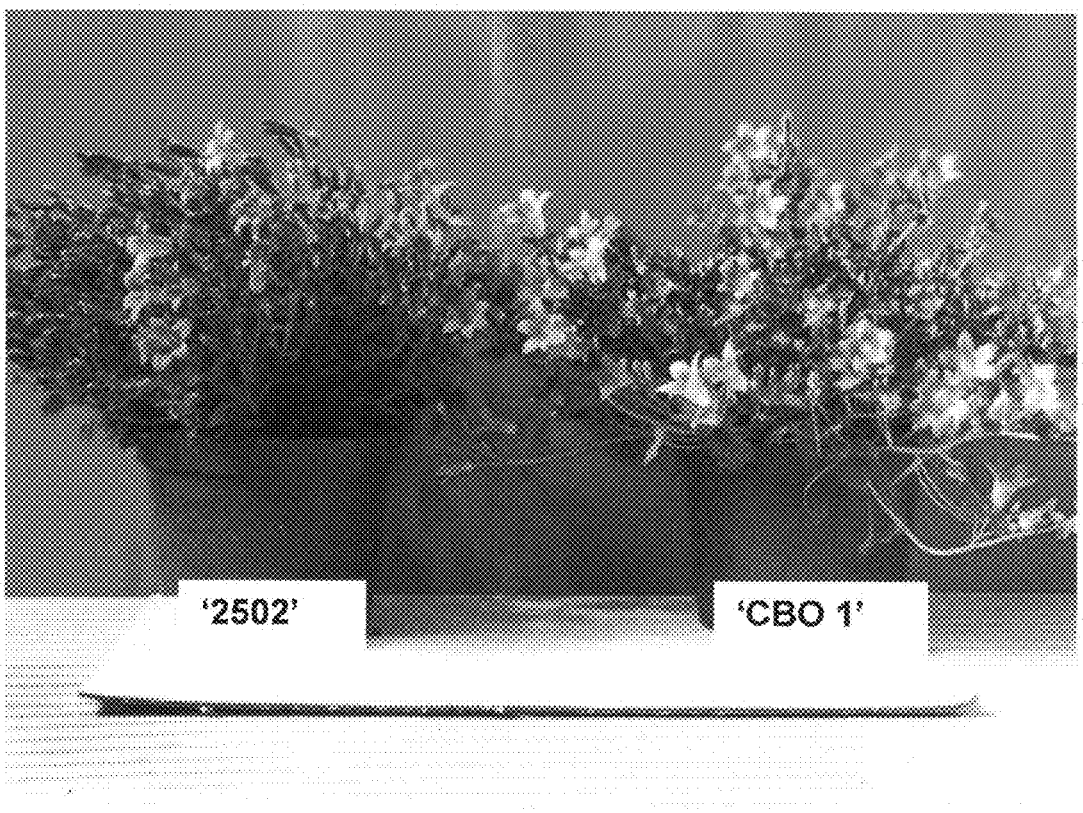
FIG. 1 shows a side perspective view of a typical flowering plant of 'CBO 1' (on right), as compared to '2502' (on left) grown in a 11 cm pot at 14 weeks of age.
Figure 2:
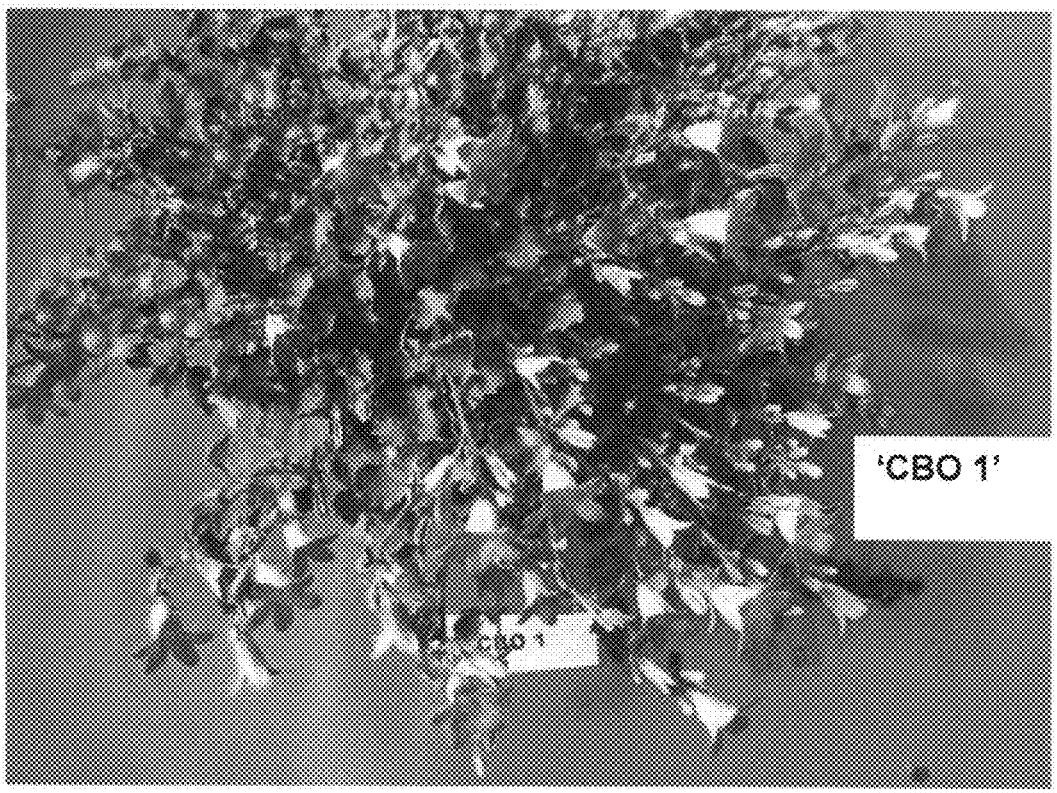
FIG. 2 shows a top perspective view of a typical flowering plant of 'CBO 1' grown in a 11 cm pot at 14 weeks of age.
Figure 3:
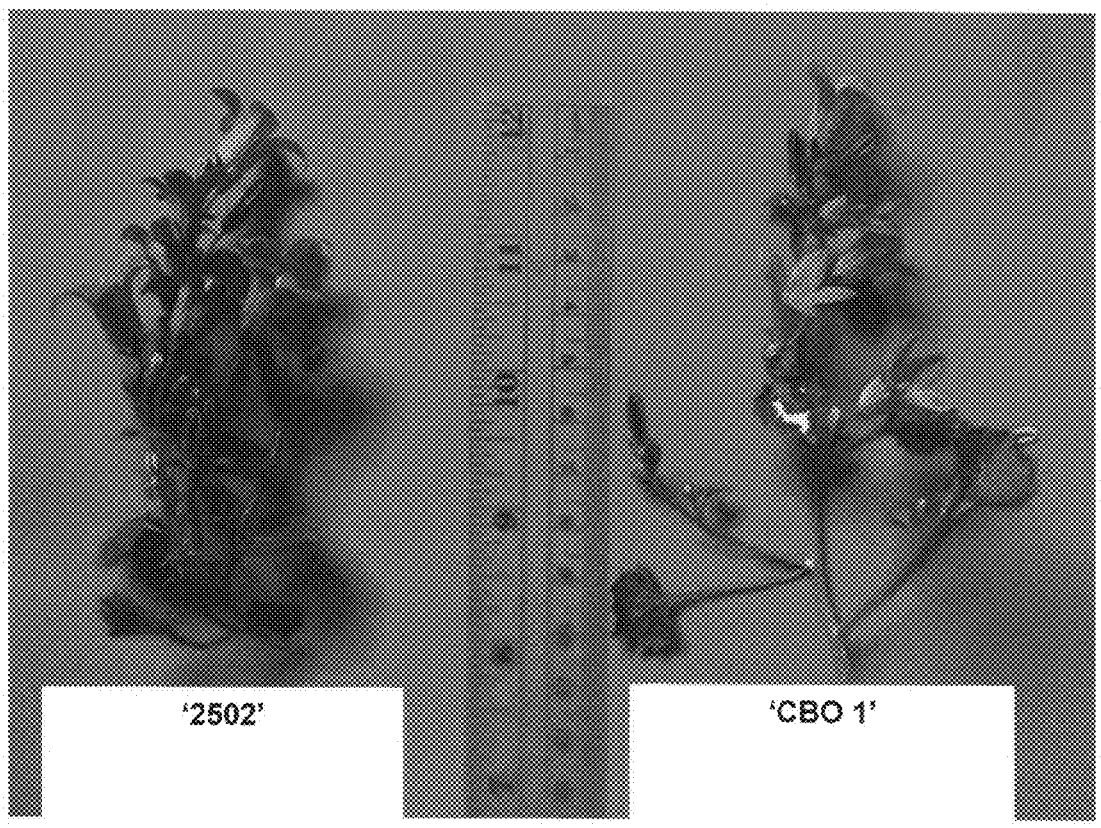
FIG. 3 shows a close-up top view perspective of a typical flowers and leaves produced by 'CBO 1' (on right) compared to '2502' (on left) at 14 weeks of age.

The new *Campanula* 'CBO 1' has not been observed under all possible environmental conditions. The phenotype of the new cultivar may vary with variations in environment such as temperature, light intensity, day length, and fertility level without any variance in genotype.

The aforementioned photographs, together with the following observations, measurements and values describe plants of the new *Campanula* 'CBO 1' as grown in a heated and lighted, glass-covered greenhouse in Fraugde, Denmark, under conditions which closely approximate those generally used in commercial practice where day and night temperatures in the greenhouse average about 18° C. Ambient light levels used while growing plants of 'CBO 1' are +40Wm$^2$. Plants of 'CBO 1' are grown with 8 hour short day photoperiodic treatments until week four, and then are grown with 18 hour long day photoperiodic treatments. Propagation and young seedling plants are exposed to 8 hour short photoperiodic treatments for about 2 weeks following planting of cutting until roots are formed. Growth retardant Bonzi (0.2%) is applied twice when growing plants of new *Campanula* 'CBO 1'.

The age of the 'CBO 1' plants described is 14 weeks old and grown in 11 cm pots. The photographs and descriptions were taken during Spring of 2009. Color references are made to The Royal Horticultural Society Colour Chart (R.H.S.), 4$^{th}$ edition, except where general colors of ordinary significance are used.

Classification: Botanical: *Campanula portenschlagiana* Schult.

Parentage: Unpatented cultivar from the proprietary breeding line of *Campanula portenschlagiana* Schult. designated '2502'.

Propagation:

*Type cutting.*—Terminal vegetative cuttings.

*Time to initiate roots.*—About 10 to 14 days at 18 to 21° C. in tunnels in a greenhouse.

*Root description.*—Fine, fibrous, well branched.

*Root color.*—Greyed-white, RHS 156B, to greyed-orange, RHS 174C.

Plant description:

*Form.*—Perennial, herbaceous, potted or bedding plant with upright to spreading plant habit. *Campanulate* flowers in racemes. Freely branching with lateral branches forming at every node; dense and bushy. Freely branching, somewhat brittle stems.

*Crop time.*—After rooting, about 14 weeks are required to produce finished flowering plants in 11 cm pots.

*Vigor.*—Vigorous growth rate.

*Plant height* (*from pot rim to top of plant plane*).—About 9 cm to 11 cm.

*Plant spread* (*width*).—About 18 cm to 21 cm.

*Lateral branches.*—Habit: Basal spreading branches, ascending center branches, and spreading to procumbent peripheral branches when flowering. Quantity: About 75 to 80 per plant. Leaves per lateral branch: About 5 to 7. Length: About 6 cm to 7 cm. Diameter: About 1 mm to 2 mm. Internode length: About 7 mm to 10 mm.

*Stem.*—Shape: Round with ridges. Strength: Stiff, somewhat brittle. Aspect: Upright and spreading. Texture: Glabrous and ridged. Color: RHS 146C, yellow-green.

Foliage description:

*Leaves.*—Arrangement: Single, alternate. Overall shape: Cordate, cup-shaped. Apex shape: Acute. Base shape: Cordate. Length: Basal: About 15 mm to 20 mm. Apical: About 5 mm to 7 mm. Width: Basal: About 14 mm to 27 mm. Apical: About 10 mm to 12 mm. Margin: Dentate, and somewhat inrolled. Texture (both sides): Smooth, glabrous, dull. Pubescence: Few, short, stiff hairs on abaxial side and along veins and indentations of margin. Foliage Color: Mature: Upper surface: Green, RHS N138A. Under Surface: Green, RHS N138B. Immature: Upper surface: Yellow-green, RHS 147C. Under Surface: Yellow-green, RHS 147D. Venation: Pattern: Palmate. Color: Upper surface: Yellow-green, RHS 146B. Under surface: Yellow-green, RHS 146D. Petiole: Basal length: About 4 cm to 6 cm. Apical length: Up to 1 cm. Diameter: 1.0 mm to 2.0 mm. Color: Yellow-green, RHS N147D. Texture: Glabrous.

Inflorescence description:

*Inflorescence arrangement and shape.*—Single, *campanulate* flowers in racemes turning upright to outward, with small, star-shaped calyx, acropetal flowering habit. Persistent.

*Natural flowering season.*—Continuous throughout spring to early summer. Season can be extended by long day treatments.

*Time to flower.*—About 6 weeks after planting of rooted cutting.

*Flower longevity.*—On the plant, flowers last up about 15 to 29 days; however, longevity of individual flowers is highly dependent on temperature and light conditions. Flowers persistent.

*Fragrance.*—None.

*Inflorescence size.*—Height: About 6 cm to 7 cm. Diameter: About 3 cm to 6 cm.

*Number of flowers per inflorescence.*—8 to 10.

*Number of flowers per lateral stem.*—2 to 4.

*Number of flowers and buds per plant.*—About 700 to 900.

*Buds.*—Length: Up to 15 mm. Diameter: Up to 4 mm. Shape: Oblong, ridged. Rate of opening: About 1 to 4 buds per day. Color: Violet, RHS N87A.

*Flowers.*—Height: About 25 to 35 mm. Diameter: About 20 mm.

*Petals.*—Arrangement: Single, sympetalous, basally fused, *campanulate.* Quantity per flower: About 5. Length: Lobes about 8 mm to 10 mm; whole petal about 14 mm to 20 mm. Width: About 7 mm. Overall Shape: Sympetalous with deltoid lobes. Tip: Acute. Base: Fused. Margin: Entire. Appearance: Shiny. Texture: Velvety. Color (when opening and fully opened): Upper surface: Tips, violet, RHS 86B; Inside base of bell, violet, RHS N87B; Fuzzy fusion lines, white, RHS N155A. Under surface: Violet, RHS N87B. Fading: Fades to violet, RHS 85D; and withers to violet-blue, RHS N89A.

*Sepals.*—Arrangement: Free, basally fused. Appearance: Dull. Quantity per flower: 5. Length: About 5 mm to 6 mm. Width: About 2 mm. Overall shape: Sagittate, arrow-shaped Tip: Cuspidate. Base: Fused. Margin: Entire. Texture: Glabrous. Color (immature): Upper surface: Yellow-green, RHS 146C; Tips, gray-purple, RHS 184B. Under surface: Yellow-green, RHS 146A; Tips, gray-purple, RHS 184B. Color (mature): Upper and under surfaces: Yellow-green, RHS 146A; Tips, greyed-purple, RHS 184B.

*Peduncles.*—Length: About 4 mm to 9 mm. Diameter: About 1 mm. Strength: Moderately strong. Color: Yellow-green, RHS 146C.

*Pedicels.*—None.

Reproductive organs:

*Androecium.*—Stamen: Quantity: 5, fused until pollen has shed. Anther: Shape: Curling after shedding. Length: About 1 mm. Color: Yellow-white, RHS 158B, with violet, RHS N87B, near tips. Pollen: Amount: Scarce. Color: Yellow-white, RHS 158B.

*Gynoecium.*—Pistil: Quantity: 1. Length: About 12 mm. Stigma: Shape: Tripartite. Color: Yellow, RHS 5A. Style: Length: About 11 mm. Color: White, RHS 155A. Ovary: Color: White, RHS 155A.

Seed/fruit: None observed.

Weather tolerance: Plants of the new *Campanula* have not been tested for tolerance to drought, rain and wind, and high temperature tolerance. Plants of the new *Campanula* exhibit low temperature resistance to −20° C. (if acclimatized).

Disease/pest resistance: Not tested.

Disease/pest susceptibility: Not tested.

I claim:

1. A new and distinct cultivar of *Campanula* plant named 'CBO 1', as illustrated and described herein.

* * * * *